United States Patent [19]

Saito et al.

[11] 4,275,243

[45] Jun. 23, 1981

[54] PROCESS FOR PRODUCING HYDROXYBUTYRALDEHYDE

[75] Inventors: Toshihiro Saito; Shoji Arai; Yukihiro Tsutsumi, all of Shin-nanyo, Japan

[73] Assignee: Toyo Soda Manufacturing Co., Ltd., Yamaguchi, Japan

[21] Appl. No.: 69,850

[22] Filed: Aug. 27, 1979

[30] Foreign Application Priority Data

Sep. 29, 1978 [JP] Japan ................................ 53-119123

[51] Int. Cl.³ ............................................. C07C 47/19
[52] U.S. Cl. ................................... 568/496; 568/454; 568/489; 568/862
[58] Field of Search .................... 260/601 R, 604 HH; 568/454, 489, 455, 496, 862

[56] References Cited

U.S. PATENT DOCUMENTS

| | | | |
|---|---|---|---|
| 3,511,880 | 5/1970 | Booth | 260/604 HF |
| 3,515,757 | 6/1970 | Silbert | 260/604 HF |
| 3,946,082 | 3/1976 | McVivker et al. | 260/604 HF |
| 4,064,145 | 12/1977 | Taylor | 568/454 |

FOREIGN PATENT DOCUMENTS

| | | | |
|---|---|---|---|
| 52-78809 | 7/1977 | Japan | 260/604 HF |
| 1493154 | 11/1977 | United Kingdom | 568/496 |

Primary Examiner—Werren B. Lone
Attorney, Agent, or Firm—Oblon, Fisher, Spivak, McClelland & Maier

[57] ABSTRACT

An organic tri-substituted phosphine having a boiling point of at least 200° C. and a reaction medium having a boiling point of at least 200° C. are used in a hydroformylation of allyl alcohol with carbon monoxide and hydrogen in the presence of a rhodium complex catalyst. The concentration of the organic phosphine is $5 \times 10^{-4}$ to 0.3 mol. per 1 liter of the reaction medium. The reaction medium is distilled at lower than 80° C. under a reduced pressure and the bottom residue as the catalyst solution is recycled. The hydroformylation can be repeated by using the bottom residue as the catalyst solution.

6 Claims, No Drawings

PROCESS FOR PRODUCING HYDROXYBUTYRALDEHYDE

BACKGROUND OF THE INVENTION

1. Field of the Invention

The present invention relates to a process for producing hydroxybutyraldehydes by reacting allyl alcohol with carbon monoxide and hydrogen in the presence of a hydroformylation catalyst containing a rhodium component.

2. Description of the Prior Art

Hydroxybutyraldehydes can be easily converted to butanediols by the known hydrogenation.

The typical compound of 1,4-butanediol is one of the important chemical compounds which has various usages such as a starting material for polymers e.g. polyesters, solvents and a starting material for syntheses.

The process for producing butanediol by using hydroxybutyraldehyde has been considered to be advantageous as an industrial process since allyl alcohol which is an economical and easily available petrochemical product.

The process for producing hydroxybutyraldehydes by reacting allyl alcohol with carbon monoxide and hydrogen in the presence of a rhodium complex having an organic tri-substituted phosphine, has been proposed in G.B. Pat. No. 1,493,154; Japanese Unexamined Patent Publication No. 78,809/1977 and U.S. Pat. No. 4,064,145.

This process has advantages in that the reaction condition is mild and the yield is high, etc. However, the process has disadvantages in that the expensive rhodium complex should be used in the process, especially, excess of the expensive organic tri-substituted phosphine should be used as the ligand. Therefore, losses of these compounds should be prevented and the separation, recovery and recycle of these compounds have been significantly important in view of the industrial operation.

The rhodium complex and the organic tri-substituted phosphine respectively have high heat stability and accordingly, it is quite advantageous to employ a distillative separation as the method of separation and recovery of the catalyst.

However, hydroxybutyraldehydes as the main reaction product in the process are thermally unstable. It is well known that hydroxybutyraldehydes are easily converted into high boiling point products by heating them in the presence of the catalyst by the reactions such as an aldol condensation and an acetalation. When the catalyst is separated from said reaction mixture to recycle the catalyst, the high boiling point product is recycled to the reaction system together with the catalyst whereby the high boiling point product is accumulated in the reaction system. It is necessary to have a step of separating the high boiling point product, in order to continue the operation. As a result, the loss or deterioration of the catalyst is sometimes caused. Thus, in the distillative separation with the heating operation, it is the most important to prevent the conversion into the high boiling point product as the reaction product.

SUMMARY OF THE INVENTION

It is an object of the present invention to overcome said disadvantages and to provide a serial process for reaction and distilled separation which attains high yield, high selectivity, the direct recycle of a catalyst solution, and the normal hydrogenation of hydroxybutyraldehydes separated by the distillation.

The foregoing and other objects of the present invention have been attained by producing hydroxybutyraldehydes by reacting allyl alcohol with carbon monoxide and hydrogen in a reaction medium in the presence of a rhodium complex catalyst having an organic tri-substituted phosphine component as a ligand, wherein an organic tri-substituted phosphine component and a reaction medium which each respectively have a boiling point of higher than 200° C. are used, and the reaction is carried out at a concentration of phosphine of $5 \times 10^{-4}$ to 0.3 mol. per/liter of the reaction medium, and a vacuum distillation is carried out at a temperature of lower than 80° C. in the absence of oxygen to separate the reaction product from the reaction medium solution of the complex catalyst.

DESCRIPTION OF THE PREFERRED EMBODIMENTS

The process of the present invention is the combination of (1) a step of hydroformylation of allyl alcohol in a reaction medium having a boiling point of higher than 200° C. in the presence of a rhodium complex catalyst having an organic tri-substituted phosphine component having a boiling point of higher than 200° C. as a ligand at a concentration of $5 \times 10^{-4}$ mol. to 0.3 mol. per 1 liter of the reaction medium; and (2) a step of vacuum distillation of the reaction medium at lower than 80° C. in the absence of oxygen to separate the object compound of hydroxybutyraldehydes from the reaction medium solution of the complex catalyst.

The reaction mixture obtained by the reaction (1) is directly fed into the distilled separation step (2) and the separated catalyst solution is recycled into the reaction system. Therefore, the reaction medium and the catalyst should be selected for the purpose of the process of the present invention and the two steps (1), (2) are mutually related each other.

The effect of the process of the present invention will be illustrated.

In the reaction step, the high yield can be given under inhibiting the formation of the high boiling point product by carrying out the reaction under the specific conditions of the present invention, such as the concentration of the organic tri-substituted phosphine. Moreover, the trouble caused by the high boiling point product in the distilled separation and the recycle of the catalyst can be prevented. Moreover, a selectivity to 4-hydroxybutyraldehyde which is especially useful as the intermediate of 1,4-butanediol is higher than 70%.

In the distillation step, the distillation is carried out in the condition of the present invention such as the vacuum distillation at a temperature of lower than 80° C. Therefore, the following four effects are given.

(1) It is possible to obtain the reaction medium solution of the catalyst component (containing large excess of phosphine) as the bottom residue and to obtain the reaction product having main components of hydroxybutyraldehydes as the object compounds as the distilled material.

(2) The distilled product can be converted into butanediols by the conventional hydrogenation.

(3) The solution of the catalyst as the bottom residue mainly comprises the catalyst component and the reaction medium without containing the high boiling point product resulted by the reaction whereby there is not the accumulation of the high boiling point product in the reaction system and the bottom residue can be continuously recycled into the reaction system without a purification.

(4) A loss of the catalyst component caused by a decomposition or a deterioration is not considered by the step of the distilled separation. The catalyst and the reaction medium are not substantially moved into the distillate. Therefore, there is no trouble in the recycling.

The process of the present invention will be further illustrated.

The rhodium complex as the hydroformylation catalyst used in the process of the present invention can be the rhodium complex used as a catalyst for hydroformylation of an olefin.

Suitable rhodium complexes include $RhH(CO)_n(PR_3)_3$; $RhX(CO)_n(PR_3)_2$; $RhX(PR_3)_3$ etc. wherein n is 1 or 2; X represents a halogen atom; $PR_3$ represents an organic tri-substituted phosphine; R represents an alkyl, aryl, alkoxy and aryloxy group and three of R in $PR_3$ can be the same or different.

The catalyst is usually used at a concentration ranging from 0.1 to 50 mg.atom preferably from 0.5 to 20 mg.atom per 1 liter of the reaction medium in view of the reaction speed and the solubility.

The tri-substituted phosphines as the ligand of the complex catalyst should have a boiling point of higher than 200° C.

The phosphines having a boiling point of higher than 200° C. can be the compound having the formula wherein a total carbon atoms of the three R is in a range of 10 to 30.

Suitable phosphines include tributylphosphine, tricyclohexylphosphine, trioctylphosphine, triphenolphosphine, tritolylphospine, methyldiphenylphosphine, ethyl-n-pentylphenylphosphine, tributoxyphosphine and triphenoxyphosphine etc.

An amount of the phosphine is usually at a ratio of 5 to 200 atoms preferably 10 to 100 atoms of phosphorus element per 1 atom of rhodium element in the complex. That is, large excess remained in the free state of the phosphine is used. Thus, the concentration of the phosphine of higher than $5 \times 10^{-4}$ mol./l. of the reaction medium is required in view of the rhodium concentration. However, when the phosphine is too much, it is unnecessary and it causes disadvantages against the object of the present invention such as the formation of a high boiling point product. Therefore, it is necessary to keep the concentration of the phosphine of less than 0.3 mol./liter preferably less than 0.25 mol./liter of the reaction medium. When the concentration of the phosphine is greater than the limit, the temperature for maintaining hydroxybutyraldehydes in stable is lowered whereby the distillation can not be practically carried out.

The reaction medium used in the present invention should have a boiling point of higher than 200° C. and is selected from the compounds having characteristics required as the reaction medium that it dissolves the catalytic component and the reaction product and it is not reactive to the catalytic component and the reaction product.

Suitable reaction media include saturated hydrocarbons having at least 12 carbon atoms such as dodecane and bicyclohexyl; aromatic hydrocarbons having at least 9 carbon atoms such as tetralin, pentylbenzene, and dodecylbenzene; alcohols having at least 9 carbon atoms such as n-nonanol and n-decanol; ethers having at least 10 carbon atoms such as dihexyl ether, butylphenyl ether and diphenyl ether; ethers or ether glycols of polyhydric alcohols having at least 7 carbon atoms such as 2-hexyloxy ethanol, 2-phenoxy ethanol, diethyleneglycol monobutyl ether, diethyleneglycol dibutyl ether and triethyleneglycol monomethyl ether; and esters having at least 9 carbon atoms such as butyl stearate, ethyl benzoate, dimethyl phthalate and 2-ethylhexyl phthalate. Two or more reaction medium can be used as a mixture.

The reaction temperature for hydroformylation in the present invention is ranging from 0° to 150° C. and preferably ranging from 20° to 80° C. in view of the thermal stability of hydroxybutyraldehydes.

The reaction pressure i.e. the pressure of the oxo gas is ranging from 1 to 50 kg./cm² as preferably ranging from 2 to 15 kg./cm² as the absolute pressure.

The composition of the oxo gas i.e. the molar ratio of hydrogen to carbon monoxide can be selected from $H_2:CO_2 = 10:1$ to $1:10$ preferably 5:1 to 1:1. An inert gas such as nitrogen and helium can be incorporated in the reaction system.

The hydroformylation product in the present invention comprises main components of 4-hydroxybutyraldehyde and 2-methyl-3-hydroxypropionaldehyde and other components of propionaldehyde and n-propanol and minor or trace of 1,4-butanediol, 2-methyl-1,3-propanediol and γ-butyrolactone; the unreacted product of allyl alcohol and the catalytic component of a rhodium complex and its ligand in a free form in the reaction medium.

The term of "hydroxybutyraldehydes" mainly means said two kinds of the aldehydes of 4-hydroxybutyraldehyde and 2-methyl-3-hydroxypropionaldehyde.

The reaction mixture obtained by the hydroformylation is separated by the distillation after purging the oxo gas. The reaction product is usually recovered from the top of the distillation tower by the distillation. On the other hand, a solution comprising the catalytic component and the reaction medium i.e. the catalyst solution is recovered and recycled into the hydroformylation without any separation. Therefore, it is important to prevent the deterioration of the reaction product in the distillation. In the process of the present invention, the reaction is carried out in the absence of oxygen gas such as an atmosphere of an inert gas e.g. $N_2$, He or Ar or a gas which does not affect to the reaction product e.g. CO and $H_2$. The reaction should be carried out at a temperature of the bottom residue of lower than 80° C. Therefore, the reaction is usually carried out in the reduced pressure.

In the separation by the distillation, the hydroxybutyraldehydes and the catalyst component are included. Therefore, when the bottom temperature is over 80° C., the hydroxybutyraldehydes is modified to decrease the yield and the high boiling point compound is accumulated in the catalyst solution whereby the purpose of the distilled separation can not be attained. On the other hand, the reaction temperature is not limited as far as it is lower than 80° C., however, in order to give a lower temperature, a high vacuum degree and excess cooling are required in the recovery of the distillate. This is not economical. Therefore, the reaction is usually carried out at a temperature of 20° to 80° C. and usually a pressure of 1–20 mmHg.

In the distillation in the process of the present invention, the usual distillation can be employed and also. For example, the reaction products having different boiling points can be separated from the reaction mixture by one step distillation or by a distillation tower having desired steps, by a single distillation or a thin layer distillation.

Moreover, it is possible to carry out the separation by the several distillations, for example, the distillation of hydroxybutyraldehydes having a relatively high boiling point after the distilled separation of lower boiling point compounds such as propionaldehyde, n-propanol and allyl alcohol, when the condition is in the above described ranges.

The hydroxybutyraldehydes obtained by the distilled separation, can be converted into butanediols by the hydrogenation in the presence of the catalyst.

The distilled products can be used for the hydrogenation without purifying them. The hydrogenation may not be disturbed even though the other reaction products are incorporated in the distilled products. The hydrogenation can be carried out by the conventional process using Raney nickel as the catalyst.

On the other hand, the bottom residue substantially comprises the catalyst component and the reaction medium and it can be recycled into the reaction system. There is no trouble in the recycling, even though a part of the reaction products such as hydroxybutyraldehydes and butanediols is remained.

The present invention will be illustrated by certain examples and references which are provided for purposes of illustration only and are not intended to be limiting the present invention.

EXAMPLE 1

In a 300 ml. autoclave made of stainless steel, 0.2 g. (0.218 mmol.) of hydridocarbonyl-tris(triphenylphosphine rhodium (hereinafter referring to as $RhH(CO)(PPh_3)_3$) and 1.14 g. (4.35 mmol.) of triphenylphosphine (hereinafter referring to as $PPh_3$) and 100 ml. of di-2-ethylhexylphthalate were charged.

The reactor was purged with a mixed gas of CO and $H_2$ (molar ratio of 1:1.2) and 230 mmol. of allyl alcohol was continuously fed for 40 minutes to react them in the mixed gas flow. The reaction was carried out during the maintenance of the reaction condition at 65° C. and under the absolute pressure of 5 kg./cm². After the addition of allyl alcohol, the same reaction condition was maintained for 20 minutes, the reaction was completed. The unreacted allyl alcohol and the reaction products in the reaction mixture or in the unreacted gas were respectively collected and analyzed by a gas chromatography. As a result, the conversion of allyl alcohol as the starting material was 98.3 mol. % and the reaction products were 169.4 mmol. of 4-hydroxybutyraldehyde (4-HBA); 22.6 mmol. of 2-methyl-3-hydroxypropionaldehyde (3-HBA); 27.1 mmol. of propionaldehyde (PrA); and 6.8 mmol. of n-propanol (PrOH) and also minor products of γ-butyrolactone (γ-BL); 1,3-butanediol (1,3-BDO) and 1,4-butanediol (1,4-BDO).

In a 300 ml. Herz flask equipped with a thermometer and a capillary, which was purged with a mixed gas of CO and $H_2$ (molar ratio of 1:1), the reaction mixture obtained by the hydroformylation was charged and the distillation was carried out at 75° C. under a reduced pressure of 3–5 mmHg. During the distillation, the contamination of oxygen was prevented by charging a mixed gas through the capillary. The distillate and the bottom residue were analyzed by a gas chromatography. The distillate comprised 164.3 mmol. of 4-HBA, 22.1 mmol. of 3-HBA, 27.0 mmol. of PrA, 6.8 mmol. of PrOH, 3.7 mmol. of the unreacted allyl alcohol and trace of γ-BL, 1,3-BDO and 1,4-BDO. On the other hand, the bottom residue comprised 5.1 mmol. of 4-HBA and 0.5 mmol. of 3-HBA and trace of γ-BL, 1,3-BDO and 1,4-BDO. As a result, no loss of the main components of 4-HBA and 3-HBA was found by the distillation.

In a 200 ml. autoclave made of stainless steel, the distillate was charged and then 33 ml. of water and 2.0 g. of Raney nickel were added. The hydrogenation was carried out at 80° C. under the hydrogen pressure of 20 kg./cm² (absolute pressure) for 2.0 hours. The resulting reaction mixture was analyzed by a gas chromatography. The reaction products comprised 164.1 mmol. of 1,4-BDO and 22.0 mmol. of 1,3-BDO. The result shows that a selectivities of allyl alcohol to butanediols were as follows.

1,4-BDO: 74.8 mol. %
1,3-BDO: 10.0 mol. %

REFERENCES 1 AND 2

In accordance with the process of Example 1, the hydroformylation was carried out in the same condition. The conversion of allyl alcohol was 98.5 mol. %.

The reaction mixture comprised 170.0 mmol. of 4-HBA, 23.1 mmol. of 3-HBA, 26.7 mmol. of PrA and 6.5 mmol. of PrOH and trace of γ-BL, 1,3-BDO and 1,4-BDO.

The reaction mixture was divided into two equal portions.

In accordance with the process of Example 1, the distillations under a reduced pressure were respectively carried out at 100° C. (22–30 mmHg) and at 125° C. (40–50 mmHg). The results are shown in Table 1. It was found that insoluble high boiling point unknown products were suspended in the bottom residue after the distillation. The content of the suspended products was greater depending upon higher temperature in the distillation.

TABLE 1

|  | Reference 1 | Reference 2 |
|---|---|---|
| Reaction temperature (°C.) | 100 | 125 |
| Distillate |  |  |
| 4-HBA (mmol.) | 82.1 | 77.4 |
| 3-HBA | 11.0 | 10.4 |
| Bottom residue |  |  |
| 4-HBA (mmol.) | 2.5 | 1.1 |
| 3-HBA | 0.3 | 0.2 |
| Loss |  |  |
| 4-HBA (%) | 0.5 | 7.6 |
| 3-HBA | 2.2 | 8.2 |

REFERENCE 3

In accordance with the process of Example 1 except using 0.6 g. of $RhH(CO)(PPh_3)_3$ and 17.1 g. of $PPh_3$ as the catalyst, the hydroformylation was carried out. The conversion of allyl alcohol was 90.0 mol. %. The reaction mixture comprised 151.7 mmol. of 4-HBA, 37.1 mmol. of 3-HBA 11.2 mmol. of PrA and 4.1 mmol. of PrOH and trace of γ-BL, 1,3-BDO and 1,4-BDO.

In accordance with the process of Example 1, the reaction mixture was distillated. The distillate comprised 144.7 mmol. of 4-HBA, 32.1 mmol. of 3-HBA, 11.0 mmol. of PrA, 3.9 mmol. of PrOH and 22.9 mmol. of the unreacted allyl alcohol and trace of γ-BL, 1,3-BDO and 1,4-BDO.

On the other hand, the bottom residue comprised 4.0 mmol. of 4-HBA, 3.3 mmol. of 3-HBA and trace of γ-BL, 1,3-BDO and 1,4-BDO and the high boiling point unknown products as described in References 1 and 2. The result shows that 2.0% of 4-HBA and 4.6% of 3-HBA were respectively converted by the distillation.

EXAMPLE 2

In accordance with the process of Example 1 except using the bottom residue obtained by the distilled separation of the reaction mixture as the catalyst solution and feeding a mixed gas of CO and $H_2$ (molar ratio of 1:1.1) the hydroformylation of 230 mmol. of allyl alcohol was carried out.

As a result, the conversion of allyl alcohol was 98.5 mol. %, to produce 170.2 mmol. of 4-HBA, 23.1 mmol. of 3-HBA, 25.3 mmol. of PrA and 7.8 mmol. of PrOH and trace of γ-BL, 1,3-BDO and 1,4-BDO.

In accordance with the process of Example 1, the reaction mixture was distilled. The distillate comprised 172.1 mmol. of 4-HBA, 22.9 mmol. of 3-HBA, 25.3 mmol. of PrA, 7.6 mmol. of PrOH and 3.4 mmol. of the unreacted allyl alcohol and trace of γ-BL and butanediols. On the other hand, the bottom residue 3.2 mmol. of 4-HBA and 0.7 mmol. of 3-HBA and were substantially the same as that of Example 1.

In accordance with the process of Example 1 the hydrogenation of the distillate was carried out to obtain 171.9 mmol. of 1,4-BDO and 22.8 mmol. of 1,3-BDO. The selectivities of the newly used allyl alcohol to butanediols were as follows.

1,4-BDO: 75.0 mol. %
1,3-BDO: 10.2 mol. %

The results show that even though the catalyst solution recovered by the distilled separation in the process of the present invention was recycled for the hydroformylation, the process for producing hydroxybutyraldehyde from allyl alcohol and the process for producing butanediols from the product can be performed without a trouble.

EXAMPLE 3

In accordance with the process of Example 2 except recycling the catalyst solution of the bottom residue recovered by the distilled separation without any purification, hydroformylation, the distilled separation and the hydrogenation were repeated for 50 times. The reaction time and the condition were not changed. The selectivities of allyl alcohol to butanediols are as follows.

1,4-BDO: 74–76 mol. %
1,3-BDO: 9–11 mol. %

What is claimed as new and intended to be secured by Letters Patent of the United States is:

1. In a process for producing hydroxybutyraldehyde by reacting allyl alcohol with carbon monoxide and hydrogen in a reaction medium in the presence of a rhodium complex catalyst having an organic tri-substituted phosphine, the improvement wherein the organic tri-substituted phosphine and the reaction medium have a boiling point higher than 200° C., the phosphine is used at a concentration of $5 \times 10^{-4}$ to 0.3 mol. per 1 liter of the reaction medium in the hydroformylation and then a distillative separation of the reaction mixture is carried out in the absence of oxygen at a temperature of 20° C. to 80° C. under a reduced pressure to separate the reaction product from the solution of the rhodium complex in the reaction medium.

2. In a process for producing hydroxybutyraldehyde by reacting allyl alcohol with carbon monoxide and hydrogen in a reaction medium in the presence of a rhodium complex catalyst having an organic trisubstituted phosphine, the improvement wherein the organic trisubstituted phosphine and the reaction medium have a boiling point higher than 200° C., the phosphine is used at a concentration of $5 \times 10^{-4}$ to 0.3 mol. per 1 liter of the reaction medium in the hydroformylation, and then a distillative separation of the reaction mixture is carried out in the absence of oxygen at a temperature lower than 80° C. and at a pressure of 1-20 mmHg, to separate the reaction product from the solution of the rhodium complex in the reaction medium.

3. The process of claims 1 or 2, wherein said rhodium complex catalyst is used at a concentration ranging from 0.1 to 15 mg atom per 1 liter of the reaction medium.

4. The process of claims 1 or 2, wherein said organic trisubstituted phosphine has the formula $PR_3$, wherein the total number of carbon atoms in the 3R's in said formula $PR_3$ is in the range of 10–30.

5. The process of claims 1 or 2, wherein the organic phosphine is used at a ratio of 5 to 200 atoms of phosphorous to 1 atom of rhodium of said catalyst.

6. The process of claims 1 or 2, wherein said reaction medium is selected from the group consisting of saturated hydrocarbons having at least 12 carbon atoms, aromatic hydrocarbons having at least 9 carbon atoms, alcohols having at least 9 carbon atoms, ethers having at least 10 carbon atoms, ether or ether glycols of polyhydric alcohols having at least 7 carbon atoms, esters having at least 9 carbon atoms, and mixtures thereof.

* * * * *